United States Patent
Rebeil et al.

(10) Patent No.: US 9,406,058 B1
(45) Date of Patent: Aug. 2, 2016

(54) SELF-SERVICE KIOSK FOR ASSAYING PRECIOUS METALS IN THE FORM OF A JEWELRY AND PAYMENT IN EXCHANGE FOR THE SAME

(71) Applicant: Blackton LLC, Newport Beach, CA (US)

(72) Inventors: Steve Rebeil, Newport Beach, CA (US); Jorge Burtin, Laguna Beach, CA (US)

(73) Assignees: Blackton, LLC., Newport Beach, CA (US); Vergent Products, Loveland, CO (US)

( * ) Notice: Subject to any disclaimer, the term of this patent is extended or adjusted under 35 U.S.C. 154(b) by 0 days.

(21) Appl. No.: 14/642,532

(22) Filed: Mar. 9, 2015

(51) Int. Cl.
| | |
|---|---|
| G06F 7/08 | (2006.01) |
| G06Q 20/20 | (2012.01) |
| G01N 33/20 | (2006.01) |
| G06Q 30/06 | (2012.01) |
| G06Q 30/02 | (2012.01) |

(52) U.S. Cl.
CPC .............. *G06Q 20/208* (2013.01); *G01N 33/20* (2013.01); *G06Q 30/0278* (2013.01); *G06Q 30/0611* (2013.01)

(58) Field of Classification Search
USPC ...................... 235/383, 381; 705/7.35; 378/46
See application file for complete search history.

(56) References Cited

U.S. PATENT DOCUMENTS

| | | | | |
|---|---|---|---|---|
| 2013/0118948 A1* | 5/2013 | Noyes | ................... | G01N 23/223 206/569 |
| 2013/0230138 A1* | 9/2013 | Jeter | ..................... | G01N 23/223 378/45 |
| 2013/0315437 A1* | 11/2013 | Kerschner | ............ | G06Q 30/018 382/100 |
| 2014/0304156 A1* | 10/2014 | Geller | ................... | G06Q 40/00 705/43 |

* cited by examiner

*Primary Examiner* — Ahshik Kim
(74) *Attorney, Agent, or Firm* — Marcus C. Dawes; Daniel L. Dawes

(57) ABSTRACT

An apparatus for automatically assaying an item made of at least one precious metal and selectively offering payment in exchange includes a user interface and control circuit; a trolley for carrying and moving the item within the apparatus; a first camera to image the item; an electronic weighing scale, and an x-ray fluorescence engine. The trolley carrying the item moves onto the weighing scale to establish a weight of the item and moves the item into the x-ray fluorescence engine to perform an x-ray fluorescence assay of the item at a location determined through image processing a visual survey of the item performed by the first camera. The user interface and control circuit creates an offer of purchase of the item based on weight and x-ray fluorescence assay of the item.

16 Claims, 3 Drawing Sheets

SELF-SERVICE KIOSK FOR ASSAYING PRECIOUS METALS IN THE FORM OF A JEWELRY AND PAYMENT IN EXCHANGE FOR THE SAME

BACKGROUND

1. Field of the Technology

The disclosure relates to the field of methods and apparatus for assaying and processing payments for items made of precious metal.

2. Description of the Prior Art

Previously, assays of items made of precious metals, such as gold, were performed at pawn shops, jewelry stores, or in mall stands by a person. The person would use some objective tests, along with their subjective experience to evaluate the item.

BRIEF SUMMARY

What is disclosed is a self-service kiosk to accept precious metals from a person, typically in the form of a jewelry item, assay the value of the item, and then offer them a payment in exchange for the item. The disclosed kiosk removes the cost, subjectivity, and errors of having an individual perform this transaction.

The primary factors to be determined in an assay for precious metals are: 1) the weight of the item, and 2) its chemical composition. Without human interaction, the disclosed kiosk can:

I. Accept an item from a customer.
II. Weigh the item.
II. Analyze the chemical makeup of the item.
IV. Make an appraisal of the item.
V. If the customer rejects the offer, the kiosk returns the item.
VI. If the customer accepts the offer, the kiosk will offer them a gift card or cash voucher at the point of sale.

The chemical analysis is done with X-ray fluorescence (XRF). XRF testing is capable of accurately determining which elements are present in a sample and in what percentages. The allows the kiosk to not only determine that a piece is gold, but whether it is 24k or 14k gold as well. In the illustrated embodiment an assay is made for gold, silver, platinum, palladium and rhodium.

The system of the illustrated embodiments accept a jewelry item in a tray configured to allow the item to be presented properly to the scale, viewing system, and XRF device. Then as needed either return the item to the user or deposit the item in a secure safe for later retrieval by authorized personnel. The system records driver license information, along with other chain of custody records such as an image of the person submitting the item, and an image of the item, to meet regulatory requirements for barter and trade of precious metals with the public.

In addition to the primary measures of weight and chemical makeup, the kiosk system has several other subsystems to make the kiosk more robust.

I. The kiosk incorporates a series of electromagnets, which provide a secondary check for ferrous content in a sample.

II. The kiosk system also has an advance illumination and image processing subsystem. This subsystem serves multiple subfunctions:

1. The imaging subsystem captures security images of both the item and the customer using the kiosk system.

2. The imaging subsystem can evaluate the size and location of the sample. From that analysis, the kiosk can make intelligent decisions on where to perform the chemical analysis.

3. The imaging subsystem can also estimate the density of the sample. The software can then verify that the density calculated based on the image, matches the chemical analysis from the XRF.

An apparatus for automatically assaying an item made of at least one precious metal and selectively offering payment in exchange for the item includes a user interface and control circuit; a trolley for carrying and moving the item within the apparatus electrically communicated with the user interface and control circuit; a first camera electrically communicated with the user interface and control circuit to image the item; an electronic weighing scale electrically communicated with the user interface and control circuit, and an x-ray fluorescence engine electrically communicated with the user interface and control circuit. The trolley carrying the item moves onto the weighing scale under the control of the user interface and control circuit to establish a weight of the item and moves the item under the control of the user interface and control circuit into the x-ray fluorescence engine to perform an x-ray fluorescence assay of the item at a location determined through image processing a visual survey of the item performed by the first camera under the control of the user interface and control circuit. The user interface and control circuit creates an offer of purchase of the item based on weight and x-ray fluorescence assay of the item.

The apparatus further includes at least one electromagnetic to test for the amount of ferromagnetic material in the item, where the electromagnetic is electrically communicated with the user interface and control circuit to be selectively operative before or after weighing of the item to determine an amount of ferromagnetic material therein.

The apparatus further includes a touchscreen electrically communicated with the user interface and control circuit to bidirectionally communicate with a live user.

The apparatus in combination with an external computer network further includes a network interface circuit to communicate the user interface and control circuit with the external computer network.

The apparatus further includes a local safe into the item is selectively deposited for safekeeping.

The apparatus further includes a second camera electrically communicated with the user interface and control circuit to photograph a user of the apparatus for storage within the user interface and control circuit in relation to the offer of purchase of the item.

The apparatus further includes a printer electrically communicated with the user interface and control circuit to print a transaction record of a complete offer of purchase.

The illustrated embodiments of the invention also contemplate a method including the steps of initiating interaction with an automatic assaying kiosk system pursuant to automatic control of the automatic assaying kiosk system where an item made of at least one precious metal is offered by a user for assay and purchase; weighing the item pursuant to automatic control of the automatic assaying kiosk system; assaying the item for purity, amount and type of precious metal or gold pursuant to automatic control of the automatic assaying kiosk system; selectively generating an offer to purchase pursuant to automatic control of the automatic assaying kiosk system; receiving and interpreting the user's response to the offer pursuant to automatic control of the automatic assaying kiosk system; and completing a transaction for purchase of the item or not according to the user's response pursuant to automatic control of the automatic assaying kiosk system.

The step of assaying the item includes assaying the item using x-ray fluorescence testing.

The method further includes the steps of imaging the item, image processing an image of the item, and determining a location on the item where assay of the item is to be performed.

The method further includes the step of magnetically testing the item to determine whether a predetermined threshold amount of ferromagnetic material in the item is exceeded.

The step of initiating interaction with the automatic assaying kiosk system includes bidirectionally communicating with the user through a touchscreen electrically communicated with a user interface and control circuit.

The method further includes the step of communicating with an external computer network pursuant to automatic control of the automatic assaying kiosk system to call for service in case of malfunction of physical handling of the item by the automatic assaying kiosk system.

The method further includes the step of selectively depositing the item when purchased into a local safe for safekeeping pursuant to automatic control of the automatic assaying kiosk system.

The method further includes the step of establishing an identity of the user including taking a photograph of the user pursuant to automatic control of the automatic assaying kiosk system.

The method further includes the step of printing a transaction record of a completed offer of purchase pursuant to automatic control of the automatic assaying kiosk system.

The method further includes the step of estimating density of the item and correlating the density to the assay of the item to determine acceptability of the item for purchase pursuant to automatic control of the automatic assaying kiosk system.

The method further includes the step of communicating with an external computer network to selectively set parameters material to generating a purchase offer pursuant to automatic control of the automatic assaying kiosk system.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
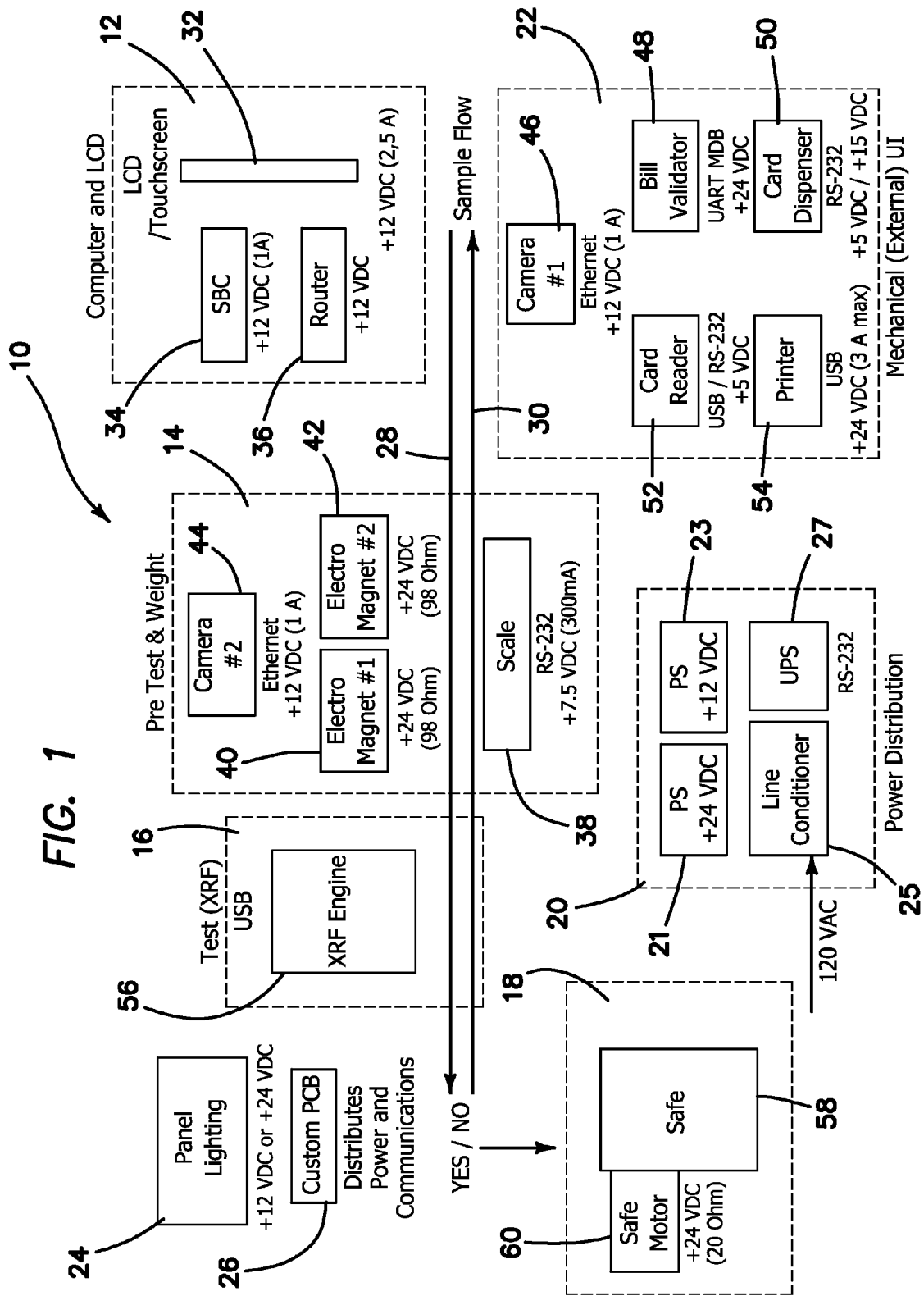
FIG. 1 is a block diagram of the primary hardware elements of the automatic kiosk system.

FIG. 1 is a block diagram illustrating the primary hardware subsystems of the kiosk system 10 of the illustrated invention. Kiosk system 10 includes a computer LCD/touchscreen module 12 communicating with a pretest and weighing module 14, an XRF module 16, a safe 18, a power distribution module 20 and a mechanical user interface module 22. Module 20 includes a plurality of DC power supplies 21, 23 providing different voltages and current services required by system 10, a line conditional 25 coupled to the external AC power and a battery powered universal power supply 27 to provide temporary power to system 10 in case of the an unexpected loss of AC power. User interface module 22 includes a camera 46 to take the photograph of the user or customer, a card reader 52 to read credit cards to take credit card payments for making the assay and/or for making electronic payments to read credit or debit card accounts for the item, a bill validator 48 to take cash payments for making the assay, a card dispenser 50 to generate gift cards for payment to the customer for the item, if elected, and a printer 54 for printing out receipts and transaction records for the customer.

Kiosk system 10 also includes a panel lighting subsystem 24 and a custom printed circuit board 26 for mounting various electronic components, including for the support of power distribution and communications.

The movement of the assayed item (not shown) within kiosk system 10 is facilitated by means of a trolley (not shown) into which the assayed item is placed by the customer. The trolley is composed of nonmagnetic material, material which does not return an appreciable x-ray signature, and has the required rigidity for use in system 10. In the illustrated embodiment the portion of the trolley in contact with and carrying the assayed item is made of blue plastic. In the illustrated embodiment it is made of polyethylene terephthalate (PET). The color blue is chosen to facilitate imaging of the item and image processing as discussed below. The movement of the trolley is symbolically shown by arrows 28, 30, which is also to be understood as symbolically representing the trolley and trolley track upon which the trolley is moved from one station to another within system 10.

The customer approaches kiosk system 10 and initiates the process as described in greater detail in connection with FIGS. 2 and 3 below by inputting information into the computer 34 through touchscreen 32 within module 12. Communication as necessary with computer 34 with external sources through computer or internet networks is facilitated by means of router 36 within module 12. A photograph of the customer is taken by camera 46 within module 22 at a selected time during the customer's interaction with kiosk system 10. The customer's photograph becomes part of the transaction record uploaded through router 36 to an external computer network, as might be required by law.

The assayed item is moved by the trolley to module 14 as symbolically shown by arrow 28 where it is weighed by scale 38 and tested by electromagnetic circuits 40, 42 to determine the extent of the item's ferromagnetic content, if any. Two electromagnetic power circuits are shown, which in turn are coupled in the illustrated embodiment to 6 electromagnets to provide sufficient coverage of the receiving area of the nonmagnetic trolley with an electromagnetic field of sufficient strength in order to carry out the magnetic test. Any number of magnets may be employed in any configuration desired to provide the testing field.

Camera 44 takes a photograph of the item, which is image processed by computer 34 to determine the preferred or best locations on the item for x-ray fluorescence (XRF) testing. X-ray fluorescence (XRF) is the emission of characteristic "secondary" (or fluorescent) X-rays from a material that has been excited by bombarding with high-energy X-rays or gamma rays. The phenomenon is widely used for elemental analysis and chemical analysis, particularly in the investigation of metals, glass, ceramics and building materials, and for research in geochemistry, forensic science and archaeology. In the illustrated embodiment, XRF engine 56 is specialized to assay heavy metals, specifically precious metals, namely gold, silver, platinum, palladium and rhodium.

Camera 44 includes a plurality of mirrors (not shown) so that images of the item in trolley are simultaneously taken to allow for estimates of the volume of the item in addition to its weight measured by scale 38, so that density can be computed by computer 34. For example, camera 44 is situated directly overhead the item in the trolley to obtain a top plan view or planar footprint of the item. The reflected views into the camera 44 from the mirrors provide orthogonal side plan views to allow volumetric measure of the item. The images are processed to determine their general shape. For example, circular or curved shapes of rings, necklaces or bracelets typically used for jewelry are recognized so that one or more locations for an XRF shot is determined for such a shaped object in order to get the best assay of the item. As discussed below the orientation of the XRF engine will be configured to take the best determined x-ray shots of the item. In the case that an anticipated shape is not detected or the shape of the item is amorphous, as might be assumed by a pile of chain, the image is processed to determine the region of largest size or mass, where preferred XRF shots will be taken.

The kind of precious metal detected and the amount in the item is communicated to computer 34, which then displays an offer of purchase to the customer. It the sale is accepted by the customer, the item is moved from the trolley into storage in a motorized safe 58 coupled to safe motor 60 in module 18. If the sale is refused by the customer, then the item is moved by the trolley back to the intake position and returned to the customer as symbolically indicated by arrow 30.

Figure 2:
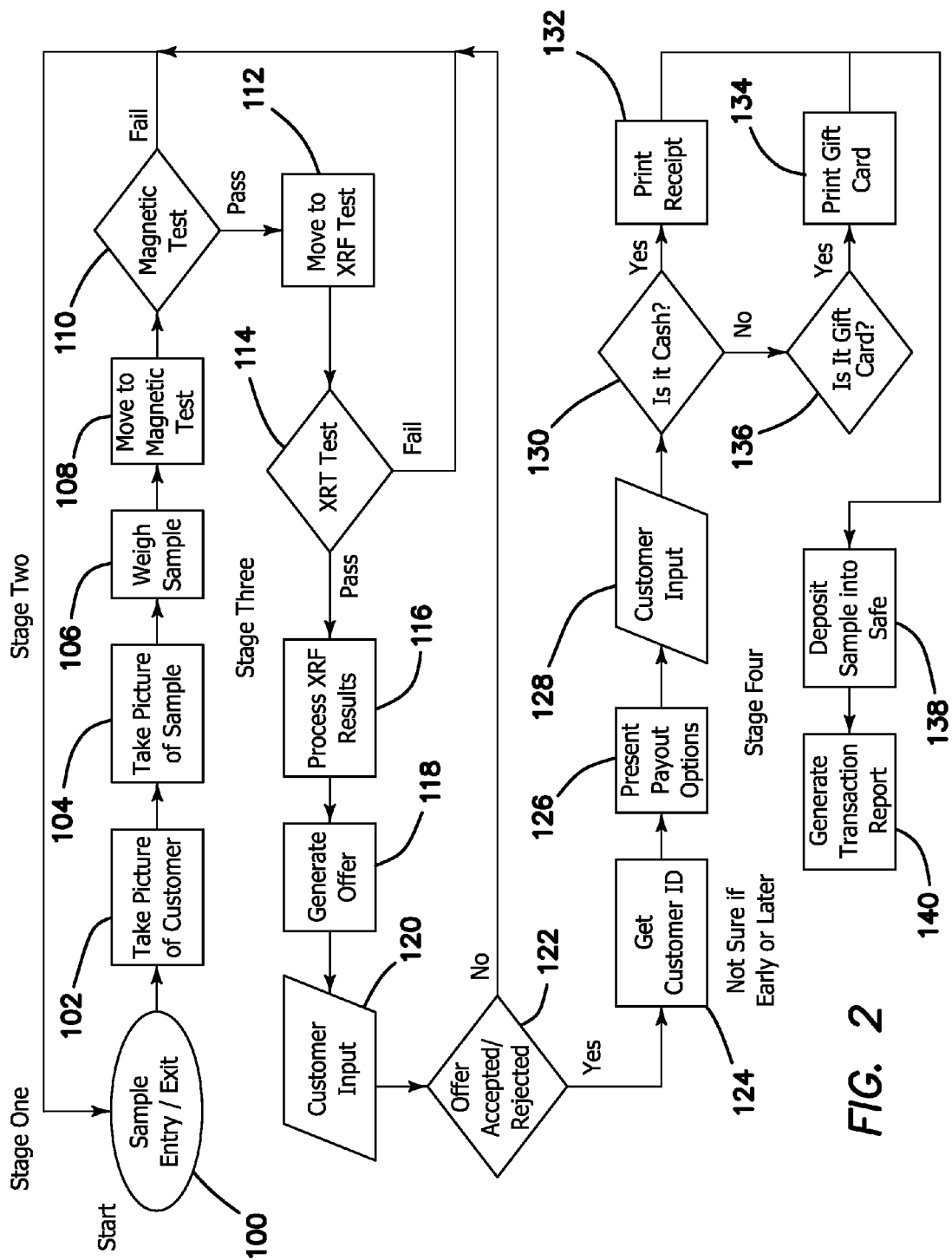
FIG. 2 is a flow diagram of an illustrated embodiment of the invention as seen largely from the viewpoint of the user's interaction leading to an assay and completed purchase transaction.
Figure 3:
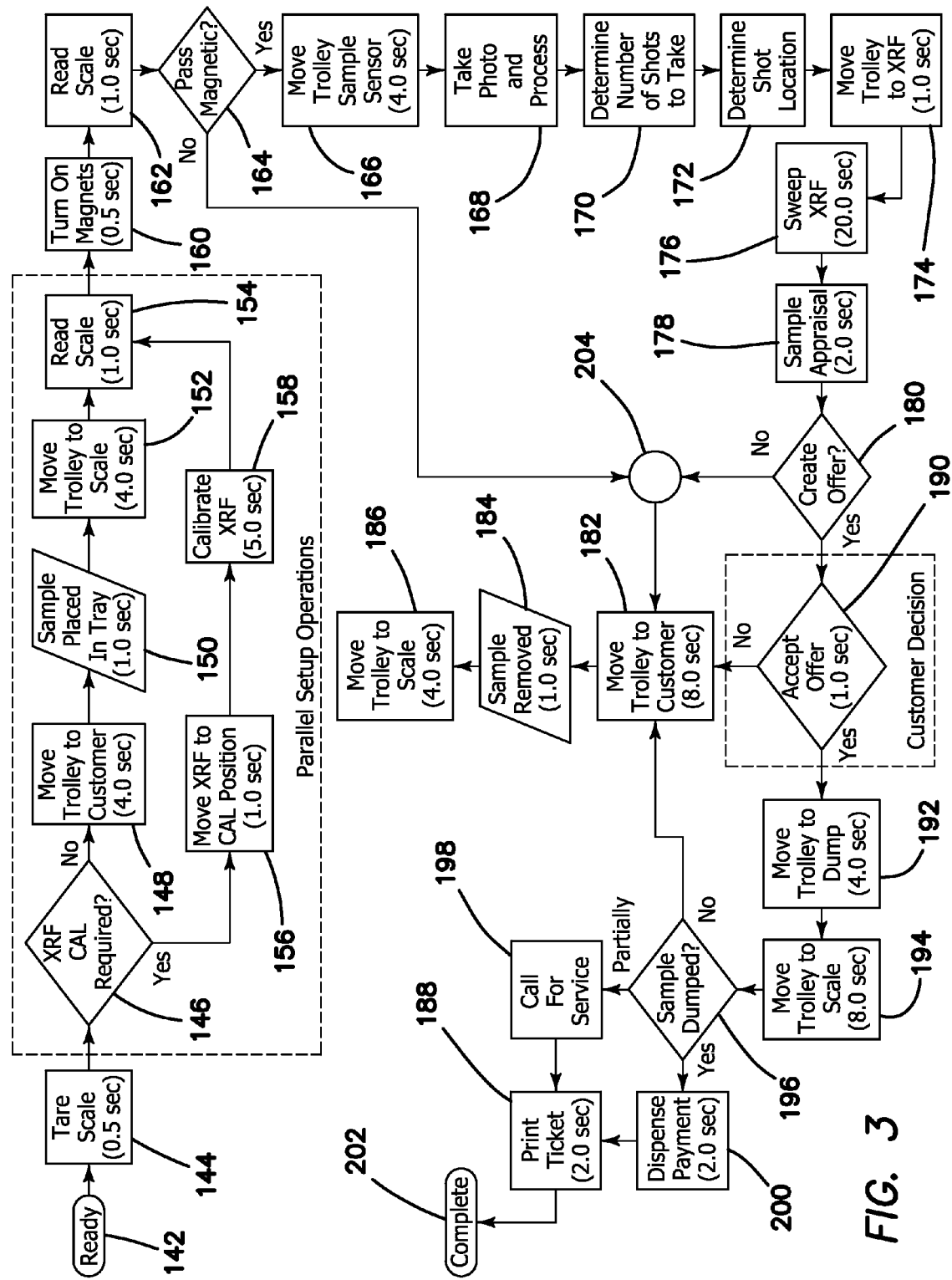
FIG. 3 is a flow diagram of an illustrated embodiment of the invention as in terms of internal kiosk operations leading to an assay and completed purchase transaction.

The modules and components of FIG. 1 can now be better and further understood by first considering the operation of kiosk system 10 as illustrated in FIGS. 2 and 3. As shown in the flow diagram of FIG. 2 the typical customer transaction begins at step 100 where the customer initiates input through touchscreen 32 of module 12 and loads the trolley through an entry portal (not shown) with the item to be assayed. The process illustrated in FIG. 2 can be envisioned as including four stages. Stage 1 is the entry phase where the item is loaded into the trolley or step 100. Stage 2 includes steps 102-110 where the customer has his or her driver's license or ID checked, payment terms for the assay determined, picture taken, the item weighed and subjected to a magnetic test. Stage 3 includes steps 112-118 is the assay stage where density and x-ray fluorescence testing for the purity, amount and type of precious metals or gold is performed and based thereon an offer is created. Stage 4 includes steps 120-140 where the customer's response to the offer is solicited and the transaction completed according to the customer's response.

Beginning then with stage 2, the language of the transaction is selected at step 101 and the payment method to be used to pay for assay is selected at step 103. If it is to be a cash transaction, then the cash is inserted at step 107 in bill validator 48 in module 22. If it is to be a credit card transaction, then card 52 is activated at step 105. In either case the terms and conditions of the transaction are displayed at step 109 to the user. If the customer rejects the terms then the processing at step 132 described below is performed. If the terms are accepted, then the customer has his or her licensed scanned at step 111, where the scanned image is emailed at step 113 to a remote computer network for automated identification and authentication or other processing. The item to be assayed is then placed in the carrier tray at step 115.

The customer's photo is taken by camera 46 at step 102, and a photograph of the item is taken at step 104, where image processing occurs in computer 34 to determine a location on the item for XRF sampling. The item is then moved by the trolley to be weighed by scale 38 in module 14 in step 106. The weight of the item is stored in the memory of computer 34. The item is then moved in step 108 to be subjected to the magnetic test at step 110, where one or both electromagnetic circuits 40 and 42 are turned on and the effect on the measured weight of the item is noted or correlated to the amount of ferromagnetic material in the item. If a weight change beyond a predetermined threshold is noted in step 110, the item returned to step 100 where it is returned to the customer in the intake tray. The threshold is set as a parameter of choice according the purchase calculus, which is programmable or can be updated by communication through router 36 with an external computer network. However, if the amount of ferromagnetic material in the item is acceptable, then it is moved in step 112 to the XRF test in step 114. If the item fails the magnetic test at step 108 then processing proceeds to step 117 for return of the item through the removal routine beginning at step 119. After the XRF test a density analysis is made at step 121 to calculate the measured density characteristics of the item. A decision is then made at step 123 whether based the item meets the predetermined parameters. If not, then the item is marked to be further processed by entering the return routine at step 117. If the density calculation returns an acceptable result, then the results are processed at step 116.

The results of the XRF test are communicated to computer 34 which determines at step 114 whether or not the purity and amount of precious metal and its type is sufficient to meet predetermined parameters stored in computer 34. If they are not sufficient, then the item is returned to step 100 for return to the customer. If the item meets the minimum parameter conditions, then results of the XRF assay and density calculation are processed at step 116 and an offer to purchase is generated by computer 34 and displayed on touchscreen 32 or printed out by printer 54 in module 22. The customer responds to the offer at step 120 through touchscreen 32. The customer's input is interpreted at step 122. If the offer is rejected, then the process returns to step 100 and the item returned to the intake tray. If the offer is accepted, then the customer is prompted by computer 34 to input his or her identification at step 124. Various payout options are then displayed at step 126 and the customer's selection of the payout option noted or input into computer 34 at step 128. If the customer has elected a cash payment as determined at step 130, printer 54 prints a cash receipt at step 132 and dispenses the cash. If the customer has elected to be paid instead by a gift card as determined at step 136, then printer 54 prints a gift card at step 134. In either the case of steps 132 or 134 the item is deposited into a safe at step 138 and a transaction report is generated to be stored in computer 34 or communicated through router 36 to a remote computer network at step 140.

Whereas FIG. 2 was a flow diagram from the viewpoint of interaction with the customer, FIG. 3 is a flow diagram of the hardware operation of kiosk system 10. The system 10 begins in the ready state at step 142. Once operation is commenced scale 38 with the empty trolley on it is read to create a tare weight at step 144 stored in computer 34, which typically takes 0.5 sec. A determination is made at step 146 whether calibration of XRF engine 56 is required. It is, then XRF engine 56 is put into the calibration configuration at step 156, which requires 1.0 sec. XRF engine 56 is then run through its self-calibration process at step 158 requiring 5.0 sec. If no calibration is required, then the trolley is moved in step 148 to the intake position in order to perform intake of the item to be assayed, which requires 4.0 sec. The item is placed in the trolley by the customer and once placed into the trolley, the trolley cycles through its intake process, such as closing the intake door, which takes 1.0 sec at step 150. The trolley then moves to the scale 38 at step 152, which takes 4.0 sec. Scale 38 is then read, weighing the weight of the item at step 154, which entails 1.0 sec. The electromagnets 40, 42 are turned on and brought up to a predetermined field strength at step 160, which takes 0.5 sec. The scale 38 is again read at step 162 within 1.0 sec. Computer 34 then makes a determination based on any weight perturbation caused by the magnets whether the amount of ferromagnetic material in the item is acceptable at step 164. If it is not, then the item is marked for return and the process moves to step 204. If the amount of ferromagnetic material in the item is acceptable, the trolley is moved to the sample sensor at step 166 taking 4.0 sec, which images the item.

The camera 44 then takes the multiple orthogonal images of the item at step 168, taking 10.0 sec. Based on the results of the composite views, the volume and density of the item is computed, and dependent on the size and shape of the item the number x-ray shots needed to determine where the assay is to be taken is made at step 170. The preferred shot location upon which is assay will be based is determined at step 172 and the XRF engine 56 is oriented relative to the position and orientation of the item in the trolley and configured to take the determined number of x-ray shots at the determined locations on the item. The trolley is then moved to the XRF engine 56 at step 174 taking 1.0 sec. XRF engine 56 sweeps through a plurality of x-ray frequencies to make a conventional assay scan at step 176 taking 20.0 seconds to complete the assay. The multiple x-ray shots at each assay location are averaged or selected if in a range considered valid, and then averaged.

Based on the XRF scan results, computer 34 appraises the item at step 178 within about 2.0 sec. Based on predetermined criterion stored in computer 34 based on the assay appraisal and market values of precious metals a specific offer for the assayed item is created at step 180. Any parameters desired, such as weight, volume, density, composition, purity, market price, percentage margins, and the like may be included in the offer calculus and/or in a acceptance or rejection decision of the item, which may be updated or modified as needed through router 36 with an external computer network operated by the kiosk owner/operator. In the illustrated embodiment, kiosk system 10 generates the purchase offer based on downloaded parameters and does not communicate on each transaction with any external computer network. However, reference to an external computer network which would perform the offer calculus is included within the scope of the invention. If it is decided by the preprogrammed algorithm not to make an offer on the item for any reason, then process flow goes to the return routine at step 204. Otherwise, an offer is presented to the customer at step 190. The customer upon viewing the offer decides whether or not to accept the offer. If the offer is not accepted, then the process moves to step 182, which is also the entry point for return routine at step 204. The trolley moves the item at step 182 taking 8.0 sec to the intake tray where the customer may retrieve it.

If the customer accepts the offer at step 190, then the trolley moves the item at step 192 to the dump position taking 8.0 sec where the trolley is tilted, motor 60 opens an upper door in safe 58, and the item dropped into the on-site safe 58. The trolley is moved to scale 38 to determine if the item has been dumped from the trolley into the safe or not at step 194 taking 8.0 sec. If the item has in fact been dumped out of the trolley at step 196, payment is dispensed at step 200 taking 2.0 sec and then a ticket or transaction record printed by printer 54 at step 188. The process will then be terminated as complete at step 202.

If the item has for any reason, not be dumped from the trolley into the safe as determined at step 196, it is moved to the customer at step 182 taking 8.0 sec. The item is returned to the customer to be removed from the trolley at step 184 within 1.0 sec. The trolley is again moved to the scale 38 at step 186 taking 4.0 sec to check that the item has in fact been removed. Thereafter, the ticket or transaction record is printed at step 188 within 2.0 sec and the process then completed.

If for any reason it has been determined at step 196 that the item has been partially removed from the trolley, but is still at least partially contributing to the weight of the trolley, an automatic service call is made at step 198 from computer 34 through router 36 to a remote network and the system 10 is shut down as temporarily inoperable. A service technician will then personally inspect system 10 to determine the cause of the malfunction and restore system 10 to an operable configuration. In the meantime, a ticket or transaction record will be printed for the customer at step 188 before shutdown of system 10 advising the customer of the malfunction and the means whereby the transaction may be completed to the customer's satisfaction.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An apparatus for automatically assaying an item made of at least one precious metal and selectively offering payment in exchange for the item comprising:
   a user interface and control circuit;
   a trolley for carrying and moving the item within the apparatus electrically communicated with the user interface and control circuit;
   a first camera electrically communicated with the user interface and control circuit to image the item;
   an electronic weighing scale electrically communicated with the user interface and control circuit, and
   an x-ray fluorescence engine electrically communicated with the user interface and control circuit,
   where the trolley carrying the item moves onto the weighing scale under the control of the user interface and control circuit to establish a weight of the item and moves the item under the control of the user interface and control circuit into the x-ray fluorescence engine to perform an x-ray fluorescence assay of the item, the user interface and control circuit creating an offer of purchase of the item based on weight and x-ray fluorescence assay of the item, and
   where the x-ray fluorescence engine is configured to perform the x-ray fluorescence at a location relative to the item that is determined by data calculated from a visual survey of the item performed by the first camera under the control of the user interface and control circuit.

2. The apparatus of claim 1 further comprising at least one electromagnetic to test for the amount of ferromagnetic material in the item, where the electromagnetic is electrically communicated with the user interface and control circuit to be selectively operative during weighing of the item to determine a weight perturbation correlating to an amount of ferromagnetic material therein.

3. The apparatus of claim 1 further comprising a touchscreen electrically communicated with the user interface and control circuit to bidirectionally communicate with a live user.

4. The apparatus of claim 1 in combination with an external computer network further comprising a network interface circuit to communicate the user interface and control circuit with the external computer network.

5. The apparatus of claim 1 further comprising a local safe into the item is selectively deposited for safekeeping.

6. The apparatus of claim 1 further comprising a second camera electrically communicated with the user interface and control circuit to photograph a user of the apparatus for storage within the user interface and control circuit in relation to the offer of purchase of the item.

7. The apparatus of claim 1 further comprising a printer electrically communicated with the user interface and control circuit to print a transaction record of a complete offer of purchase.

8. A method comprising:
   initiating interaction with an automatic assaying kiosk system pursuant to automatic control of the automatic assaying kiosk system where an item made of at least one precious metal is offered by a user for assay and purchase;
   weighing the item pursuant to automatic control of the automatic assaying kiosk system;
   assaying the item for purity, amount and type of precious metal or gold pursuant to automatic control of the automatic assaying kiosk system;
   selectively generating an offer to purchase pursuant to automatic control of the automatic assaying kiosk system;
   receiving and interpreting the user's response to the offer pursuant to automatic control of the automatic assaying kiosk system; and
   completing a transaction for purchase of the item or not according to the user's response pursuant to automatic control of the automatic assaying kiosk system,
   where assaying the item for purity, amount and type of precious metal or gold pursuant to automatic control of the automatic assaying kiosk system comprises performing x-ray fluorescence at a location relative to the item that is determined by data calculated from a visual survey of the item performed by a camera under the automatic control of the automatic assaying kiosk system.

9. The method of claim 8 further comprising selectively operating at least one electromagnetic during weighing of the item to determine a weight perturbation correlating to an amount of ferromagnetic material therein and comparing the correlated amount of ferromagnetic material to a predetermined threshold amount of ferromagnetic material.

10. The method of claim 8 where initiating interaction with the automatic assaying kiosk system comprises bidirectionally communicating with the user through a touchscreen electrically communicated with a user interface and control circuit.

11. The method of claim 8 further comprising communicating with an external computer network pursuant to automatic control of the automatic assaying kiosk system to call for service in case of malfunction of physical handling of the item by the automatic assaying kiosk system.

12. The method of claim 8 further comprising selectively depositing the item when purchased into a local safe for safekeeping pursuant to automatic control of the automatic assaying kiosk system.

13. The method of claim 8 further comprising establishing an identity of the user including taking a photograph of the user pursuant to automatic control of the automatic assaying kiosk system.

14. The method of claim 8 further comprising printing a transaction record of a completed offer of purchase pursuant to automatic control of the automatic assaying kiosk system.

15. The method of claim 8 further comprising estimating density of the item and correlating the density to the assay of the item to determine acceptability of the item for purchase pursuant to automatic control of the automatic assaying kiosk system.

16. The method of claim 8 further comprising communicating with an external computer network to selectively set parameters material to generating a purchase offer pursuant to automatic control of the automatic assaying kiosk system.

\* \* \* \* \*